(12) United States Patent
Sardesai et al.

(10) Patent No.: US 10,994,099 B2
(45) Date of Patent: *May 4, 2021

(54) DEVICES, SYSTEMS, AND METHODS FOR DELIVERING CATHETERS OR OTHER MEDICAL DEVICES TO LOCATIONS WITHIN A PATIENTS BODY

(71) Applicants: Rajendra Gurudas Sardesai, Arcadia, CA (US); Samir Bipin Pancholy, Clarks Summit, PA (US)

(72) Inventors: Rajendra Gurudas Sardesai, Arcadia, CA (US); Samir Bipin Pancholy, Clarks Summit, PA (US)

(73) Assignee: VASOINNOVATIONS INC., South Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/017,228

(22) Filed: Sep. 10, 2020

(65) Prior Publication Data

US 2021/0046286 A1 Feb. 18, 2021

Related U.S. Application Data

(63) Continuation of application No. 16/676,373, filed on Nov. 6, 2019, now Pat. No. 10,792,469.
(Continued)

(51) Int. Cl.
*A61M 25/01* (2006.01)
*A61M 25/10* (2013.01)
(Continued)

(52) U.S. Cl.
CPC ...... *A61M 25/0147* (2013.01); *A61M 25/005* (2013.01); *A61M 25/0071* (2013.01);
(Continued)

(58) Field of Classification Search
CPC .............. A61M 25/10; A61M 25/0071; A61M 25/1006; A61M 25/1009; A61M 25/1011;
(Continued)

(56) References Cited

U.S. PATENT DOCUMENTS 4,294,233 A 10/1981 Takahashi
4,425,919 A 1/1984 Alston et al.
(Continued)

FOREIGN PATENT DOCUMENTS

DE 102017118468 A1 2/2019
EP 0885624 A2 12/1998
(Continued)

OTHER PUBLICATIONS

Search History in International application No. PCT/US2020/041743.
Written Opinion of the International Searching Authority in International application No. PCT/US2020/041743.
International Search Report in International application No. PCT/US2020/041743.
(Continued)

*Primary Examiner* — Tiffany Legette
(74) *Attorney, Agent, or Firm* — Rajendra Gurudas Sardesai

(57) ABSTRACT

Devices, systems, and methods are disclosed that help deliver catheters or other medical devices to locations within a patient's body. The device includes a transporter catheter having a proximal end and a distal end, at least a first balloon located at the distal end, substantially at a tip of the transporter catheter, and at least a second balloon located between the distal end and the proximal end of the transporter catheter. The first balloon is an orienting balloon and the second balloon is an anchor balloon. The transporter catheter may include a single lumen or more than one lumen. The transporter catheter may have a shaft including an inner
(Continued)

layer and an outer layer, the inner layer may be made of a material more flexible than the material of the outer layer. The outer layer may also include a braided wire assembly, said braided wire assembly being formed by braiding a plurality of flat wires or circular wires. The braided wire assembly may wrap around the inner layer. The transporter catheter may have a shaft that may include a plurality of segments of varying degrees of hardness. The degree of hardness of the segment of the shaft of the transporter catheter located between the first balloon and the second balloon may be less than the degree of hardness of the segment of the shaft between the second balloon and the proximal end of the catheter.

20 Claims, 19 Drawing Sheets

Related U.S. Application Data

(60) Provisional application No. 62/886,349, filed on Aug. 14, 2019.

(51) Int. Cl.
  A61M 25/00 (2006.01)
  A61M 25/09 (2006.01)
  A61M 25/02 (2006.01)

(52) U.S. Cl.
  CPC ........ A61M 25/0108 (2013.01); A61M 25/09 (2013.01); A61M 25/1009 (2013.01); A61M 25/1011 (2013.01); A61M 25/0155 (2013.01); A61M 2025/0293 (2013.01); A61M 2025/09008 (2013.01); A61M 2025/09133 (2013.01)

(58) Field of Classification Search
  CPC .......... A61M 25/0662; A61M 25/0147; A61M 25/065; A61M 2025/1013; A61M 2025/1015; A61M 2025/0681; A61M 2025/0656; A61M 2025/1059; A61M 2025/1061; A61M 2025/1043; A61M 2025/0687
  See application file for complete search history.

(56) References Cited

U.S. PATENT DOCUMENTS

| | | |
|---|---|---|
| 4,757,827 A | 7/1988 | Buchbinder et al. |
| 5,167,221 A | 12/1992 | Chikama |
| 5,271,415 A | 12/1993 | Foerster et al. |
| 5,395,329 A | 3/1995 | Fleischhacker et al. |
| 5,441,483 A | 8/1995 | Avitall |
| 5,456,664 A | 10/1995 | Heinzelman et al. |
| 5,472,017 A | 12/1995 | Kovalcheck |
| 5,637,086 A | 6/1997 | Ferguson et al. |
| 5,827,278 A | 10/1998 | Webster |
| 5,876,375 A | 3/1999 | Penny |
| 5,906,606 A * | 5/1999 | Chee .................. A61M 25/005 604/527 |
| 6,027,462 A | 2/2000 | Greene et al. |
| 6,143,013 A | 11/2000 | Samson et al. |
| 6,146,338 A | 11/2000 | Gardeski et al. |
| 6,179,809 B1 | 1/2001 | Khairkhahan et al. |
| 6,190,333 B1 | 2/2001 | Valencia |
| 6,394,976 B1 | 5/2002 | Winston et al. |
| 6,432,112 B2 | 8/2002 | Brock et al. |
| 6,450,948 B1 | 9/2002 | Matsuura et al. |
| 6,485,455 B1 | 11/2002 | Thompson |
| 6,530,897 B2 | 3/2003 | Nardeo |
| 6,533,783 B1 | 3/2003 | Tollner |
| 6,582,536 B2 | 6/2003 | Shimada |
| 6,607,496 B1 | 8/2003 | Poor et al. |
| 6,991,616 B2 | 1/2006 | Bencini et al. |
| 7,077,823 B2 | 7/2006 | McDaniel |
| 7,331,980 B2 | 2/2008 | Dubrul et al. |
| 7,377,906 B2 | 5/2008 | Selkee |
| 7,494,478 B2 | 2/2009 | Itou et al. |
| 7,691,095 B2 | 4/2010 | Bednarek et al. |
| 7,766,868 B2 | 8/2010 | Goode et al. |
| 7,914,515 B2 | 3/2011 | Heideman et al. |
| 8,206,371 B2 | 6/2012 | Nimkar et al. |
| 8,292,850 B2 | 10/2012 | Root et al. |
| 8,313,478 B2 | 11/2012 | Tockman et al. |
| 8,313,493 B2 | 11/2012 | Fischer |
| 8,323,239 B2 | 12/2012 | Bednarek et al. |
| 8,603,066 B2 | 12/2013 | Heideman et al. |
| 8,702,625 B2 | 4/2014 | Ayala et al. |
| 8,734,699 B2 | 5/2014 | Heideman et al. |
| 8,747,428 B2 | 6/2014 | Fischell et al. |
| 8,814,825 B2 | 8/2014 | Tegg et al. |
| 8,858,528 B2 | 10/2014 | Sicvol |
| 8,926,560 B2 | 1/2015 | Dinh et al. |
| 9,259,813 B2 | 2/2016 | Heideman et al. |
| 9,320,503 B2 | 4/2016 | Bolduc |
| 9,492,636 B2 | 11/2016 | Heideman et al. |
| 9,681,882 B2 | 6/2017 | Garrison |
| 9,763,784 B2 | 9/2017 | Bielefeld |
| 9,764,118 B2 | 9/2017 | Anderson et al. |
| 9,788,943 B2 | 10/2017 | Deshmukh et al. |
| 9,987,463 B2 | 6/2018 | Guo et al. |
| 10,004,877 B2 | 6/2018 | Tegg |
| 10,035,000 B2 | 7/2018 | Bednarek et al. |
| 10,058,677 B2 | 8/2018 | Kawase |
| 10,099,036 B2 | 10/2018 | Heideman et al. |
| 10,130,791 B2 | 11/2018 | Heideman et al. |
| 10,182,841 B1 | 1/2019 | Rousu et al. |
| 10,194,905 B2 | 2/2019 | Bolduc et al. |
| 10,478,296 B2 | 11/2019 | Le et al. |
| 10,517,721 B2 | 12/2019 | Taylor |
| 10,653,862 B2 | 5/2020 | Winston et al. |
| 2002/0013580 A1 | 1/2002 | Houser |
| 2002/0026145 A1 | 2/2002 | Bagaoisan et al. |
| 2002/0087156 A1 | 7/2002 | Maguire et al. |
| 2002/0111649 A1 | 8/2002 | Russo et al. |
| 2002/0165598 A1 | 11/2002 | Wahr et al. |
| 2003/0004541 A1 | 1/2003 | Linder et al. |
| 2003/0105451 A1 | 6/2003 | Westlund et al. |
| 2003/0149467 A1 | 8/2003 | Linder et al. |
| 2003/0199963 A1 | 10/2003 | Tower et al. |
| 2004/0002706 A1 | 1/2004 | Houser |
| 2004/0064179 A1 | 4/2004 | Linder et al. |
| 2004/0073158 A1 | 4/2004 | Shah et al. |
| 2004/0143256 A1 | 7/2004 | Bednarek |
| 2004/0193055 A1 | 9/2004 | Field et al. |
| 2004/0220549 A1 | 11/2004 | Dittman et al. |
| 2005/0059965 A1 | 3/2005 | Eberl et al. |
| 2005/0107737 A1 | 5/2005 | McDaniel |
| 2006/0106375 A1 | 5/2006 | Werneth et al. |
| 2006/0241564 A1 | 10/2006 | Corcoran et al. |
| 2007/0005008 A1 | 1/2007 | Honebrink et al. |
| 2007/0005131 A1 | 1/2007 | Taylor |
| 2007/0112369 A1 | 5/2007 | Crossman |
| 2007/0173757 A1 | 7/2007 | Levine et al. |
| 2007/0225677 A1 * | 9/2007 | Rowe ................ A61M 25/1011 604/509 |
| 2007/0270679 A1 | 11/2007 | Nguyen |
| 2008/0183128 A1 | 7/2008 | Morriss et al. |
| 2008/0281228 A1 | 11/2008 | Parodi et al. |
| 2009/0062602 A1 | 3/2009 | Rosenberg et al. |
| 2011/0301502 A1 | 12/2011 | Gill |
| 2012/0053419 A1 | 3/2012 | Bloom |
| 2012/0116353 A1 | 5/2012 | Arnold et al. |
| 2012/0157913 A1 | 6/2012 | Aziz et al. |
| 2013/0237962 A1 | 9/2013 | Kawai |
| 2014/0005647 A1 | 1/2014 | Shuffler et al. |
| 2014/0058251 A1 | 2/2014 | Stigall et al. |
| 2014/0155980 A1 | 6/2014 | Turjman et al. |
| 2014/0180086 A1 | 6/2014 | Jang et al. |
| 2014/0276618 A1 | 9/2014 | Di Caprio et al. |

(56) References Cited

U.S. PATENT DOCUMENTS

| | | |
|---|---|---|
| 2015/0051634 A1* | 2/2015 | Kravik .............. A61M 25/1034 606/194 |
| 2015/0196740 A1 | 7/2015 | Mallin et al. |
| 2015/0265806 A1 | 9/2015 | Kawaguchi |
| 2015/0265812 A1 | 9/2015 | Lalonde et al. |
| 2016/0051799 A1* | 2/2016 | Daniels .............. A61M 25/1011 604/101.01 |
| 2016/0114126 A1 | 4/2016 | Heideman et al. |
| 2016/0249942 A1 | 9/2016 | Olson |
| 2016/0346515 A1 | 12/2016 | Buller et al. |
| 2016/0361058 A1 | 12/2016 | Bolduc et al. |
| 2017/0028170 A1 | 2/2017 | Ho |
| 2019/0255297 A1 | 8/2019 | Fischell et al. |
| 2019/0255299 A1 | 8/2019 | Fischell et al. |
| 2020/0085483 A1 | 3/2020 | Tegg et al. |

FOREIGN PATENT DOCUMENTS

| | | |
|---|---|---|
| EP | 1676595 A1 | 7/2006 |
| EP | 3037122 A1 | 6/2016 |
| EP | 2670355 B1 | 11/2016 |
| EP | 2349086 B1 | 3/2017 |
| EP | 2869882 B1 | 2/2018 |
| JP | 2000033122 A | 2/2000 |
| WO | WO2000067834 A1 | 11/2000 |
| WO | WO 02/05868 A2 | 1/2002 |

OTHER PUBLICATIONS

Tejas Patel, et al,"Balloon-Assisted Tracking of a Guide Catheter Through Difficult Radial Anatomy: A Tech. Report" Catheterization and Cardiovasc Intervent. 81:E215-8 (2013).

Tejas Patel, et al,"Balloon-Assisted Tracking: A Must Know Technique to Overcome Difficult Anatomy During Transradial Approach" Cath and Cardiovasc Intervent. 83:E211-20(2014).

International Search Report in International application No. PCT/US 20/29999.

Written Opinion of the International Searching Authority in International application No. PCT/US 20/29999.

Search History in International application No. PCT/US 20/29999.

Extended European Search Report EESR Application No. EP 20 17 2795.

* cited by examiner

DEVICES, SYSTEMS, AND METHODS FOR DELIVERING CATHETERS OR OTHER MEDICAL DEVICES TO LOCATIONS WITHIN A PATIENTS BODY

CROSS-REFERENCE TO RELATED APPLICATIONS

This application is a continuation of co-pending U.S. patent application Ser. No. 16/676,373 filed Nov. 6, 2019 which is a non-provisional of U.S. Provisional Application No. 62/886,349, filed Aug. 14, 2019, the entire content of which is incorporated herein by reference.

FIELD OF THE INVENTION

The invention relates generally to devices, systems, and methods that help deliver catheters or other medical devices to locations within a patient's body. More particularly, the present invention is directed to a transporter catheter, which is located inside an outer catheter, e.g. a sheath, an introducer catheter, a guide catheter or an inner catheter. An orienting balloon at a tip of the transporter catheter assists in the orientation and positioning of the transporter catheter, and an anchor balloon is used for anchoring the transporter catheter, e.g. anchoring the transporter catheter to an inner surface of a sheath or an introducer catheter or a guiding catheter or an inner catheter as the user maneuvers the system comprising the transporter catheter and the sheath or the introducer catheter or the guiding catheter through the patient's body.

BACKGROUND OF THE INVENTION

Catheters are used for an ever-growing number of medical procedures including diagnostic and/or therapeutic procedures. To facilitate placement of the diagnostic and/or therapeutic catheter at a location of interest within a patient, a catheter may be introduced through a second catheter, which is commonly known as a "sheath" or "introducer catheter," and these two terms will be used interchangeably herein. An introducer catheter is a tube that is used to facilitate the placement of other catheters into specific areas of the patient's body. In the field of cardiac ablation, for example, introducer catheters may be used to negotiate the patient's vasculature such that an ablation device may be passed through and positioned to be able to ablate arrhythmia-causing cardiac tissue. The introducer catheter itself may be advanced over a guide wire.

Complex coronary anatomy including tortuosity, calcification, as well as other structural characteristics of the coronary artery can make transit of hardware through the lumen proximal to a stenosis difficult and sometimes impossible. Several advancements in technology such as stiffer guide wires, large bore guide catheters that allow for improved passive support, hydrophilic coating allowing for reduced friction, have improved the ability to advance balloons and stents through these diseased and difficult coronary arteries with some success. Guide wires that allow for dynamic deflection of the tip such as the "Wiggle" wire have also improved hardware transit. However, even with these advances, in view of the expanding indications for percutaneous coronary intervention ("PCI"), there is an unmet need for improving PCI outcomes in complex substrates.

A guide catheter may be located inside an introducer catheter, and an inner support catheter ("daughter" or "child" catheter) placed inside a guide catheter. Advancing the inner support catheter into the coronary artery deeply intubating the proximal coronary artery lumen has been shown to improve support of the guide catheter and inner catheter composite system, thereby providing an opportunity for improved success for device advancement through a difficult coronary lumen (Guideliner, Guidezilla, Telescope). Frequently, these inner catheters are only able to navigate the proximal simpler portions of the artery anatomy, and do not allow the operator to obtain a position in the artery lumen that provides sufficient support. The lack of ability to advance these inner catheters is frequently as a result of the "razor effect" caused by an overhang or transitions between the guidewire and the inner support catheter.

Generally, it is known that the introducer catheter must have an overall diameter small enough to negotiate through a lumen of a vessel while retaining an inner diameter (or "bore size") large enough to accommodate a diagnostic, a therapeutic and/or an ablation device therethrough. Furthermore, since the path within a patient's vessel is often long and tortuous, steering forces must be transmitted over relatively long distances. Accordingly, it is desirable for the introducer catheter to have enough axial strength to be pushed through the patient's vasculature via a force applied at its proximal end ("pushability"). It is also desirable for the introducer catheter to be capable of transmitting a torque applied at the proximal end through to the distal end ("torqueability"). An introducer catheter should also have enough flexibility to conform substantially to the patient's vasculature and yet resist kinking as it conforms to the patient's vasculature. These various characteristics are often in conflict with one another, with improvements in one often requiring compromises in others. For example, increasing the bore size of an introducer catheter having a given overall diameter requires utilizing a thinner wall. As catheters are used in smaller and smaller passages, there is a growing need to use introducer catheters that have a smaller outer dimension. However, a thin-walled introducer catheter is more likely to collapse upon itself or kink when a torque or a push force is applied at its proximal end.

In order to facilitate the advancement of an introducer catheter (or an introducer sheath) through a patient's vasculature, the application of a push force and/or torque at the proximal end of the introducer catheter and the ability to orient selectively the distal tip of the introducer catheter in a desired direction can permit medical personnel to advance the distal end of the catheter and to position the distal portion of the introducer catheter at a location of interest.

During use, an introducer catheter shaft should be capable of transmitting torque and resisting compression. Substantial frictional forces sometimes resist transmission of axial forces and torque along the length of the introducer catheter. In some cases, these forces may cause the introducer catheter shaft to twist about a longitudinal axis of the introducer catheter shaft, storing energy in the process in a spring-like fashion. If such energy is released suddenly, the distal end of the introducer catheter, which may have been deflected by a steering mechanism, may be undesirably propelled with significant force.

With respect to resisting compression during use, it is important that users be able to advance the introducer catheter through a vessel, sometimes against significant frictional resistance, without undue axial or radial compression or snaking or fish-mouthing of the introducer catheter shaft. Shaft compression may complicate the positioning of the distal end of the introducer catheter shaft at a desired location for a medical procedure. In addition, medical personnel may rely on tactile feedback to attain and verify proper positioning of the introducer catheter, and such feedback can be impaired by excessive compressibility.

Accordingly, there is a need for improved devices, systems and methods to deliver an introducer catheter or a sheath or a guide catheter or an inner catheter at a location of interest within a patient's body via a body lumen without damaging the lumen, or a body vessel, including a tortuous lumen or vessel. The foregoing discussion is intended only to illustrate the present field and should not be taken as a disavowal or limitation of claim scope.

SUMMARY OF THE INVENTION

The devices, systems, and methods for negotiating a patient's vasculature through lumens or vessels are described herein. In particular, the present invention provides improved devices, systems, and methods for procedures including diagnostic, therapeutic, and ablative procedures in arterial and venous systems, as well as for nonvascular lumen. A catheter system of the present invention comprises a transporter catheter and an introducer catheter. In an exemplary embodiment, a balloon at a distal tip of a transporter catheter facilitates the negotiation of the transporter catheter and/or associated device or system through the body lumens of a patient. The transporter catheter may have at least one anchor balloon that anchors the transporter catheter to the introducer catheter. The anchor balloon prevents slippage or "pushback" of the transporter catheter backwards into the lumen of the introducer catheter when the orienting balloon of the transporter catheter experiences increased resistance within the vasculature in the patient's body. Also, when the anchoring balloon is located proximate to the orienting balloon, the anchoring balloon acts as a stopper to prevent the orienting balloon from backing into the lumen of the introducer catheter as the catheter system is being maneuvered through the vasculature of the patient's body. It also prevents the orienting balloon from migrating fully out of the introducer catheter, guide catheter or inner catheter when forward force is applied to the catheter system. In the description of the invention, the transporter catheter is described as being located inside the introducer catheter. The transporter catheter may also be located inside any outer catheter, e.g., a sheath, a mother catheter, a guiding catheter or a daughter catheter, to advance the outer catheter. An orienting balloon at a tip of the transporter catheter assists in the orientation and positioning of the transporter catheter, and an anchor balloon is used for anchoring the transporter catheter, e.g., anchoring the transporter catheter to an inner surface of an outer catheter as the user maneuvers the system comprising the transporter catheter and the outer catheter through the patient's body. The description and discussion regarding advancing the introducer catheter also applies to advancing any other catheter through a patient's vasculature using a transporter catheter.

The catheter system of the present invention may be advanced through the vasculature of a patient's body by (a) pushing and/or torqueing the introducer catheter, (b) pushing and/or torqueing the transporter catheter, or (c) pushing and/or torqueing both the introducer catheter and the transporter catheter. If the user pushes and/or torques the introducer catheter to advance the catheter system through the vasculature of the patient's body, then the anchor balloon of the transporter catheter pushes and/or torques the transporter catheter as the catheter system moves through the vasculature of the patient's body. If the user pushes and/or torques the transporter catheter to advance the catheter system through the vasculature of the patient's body, the anchor balloon of the transporter catheter pulls and/or torques the introducer catheter as the catheter system moves through the vasculature of the patient's body. In both cases, the orienting balloon assists in orienting and maneuvering the catheter system through the vasculature of the patient's body.

An embodiment of the invention provides devices, systems, and methods including a transporter catheter comprising a first tube having a length and defining a first open interior lumen, the first open interior lumen connected to a first balloon located at a distal end of the transporter catheter, a second tube having a length and defining a second open interior lumen, the second open interior lumen connected to a second balloon located between the first balloon and the proximate end of the transporter catheter. In another embodiment, the second balloon is proximate to the first balloon. In yet another embodiment, the distance between the proximal end of the first balloon and the distal end of the second balloon is less than half the width of the fully inflated first balloon. In another embodiment, the distance between the proximal end of the first balloon and the distal end of the second balloon is less than half the diameter of the fully inflated first balloon.

In another embodiment of the invention, the device comprises a transporter catheter having a proximal end and a distal end, at least a first balloon located at the distal end, substantially at a tip of the transporter catheter, and at least a second balloon located between the distal end and the proximal end of the transporter catheter. The first balloon is an orienting balloon and the second balloon is an anchor balloon. The transporter catheter may include a single lumen or more than one lumen. The shaft of the transporter catheter may comprise an inner layer and an outer layer, the inner layer may be made of a material more flexible than the material of the outer layer. The outer layer may also comprise braided wire assembly, said braided wire assembly being formed by braiding a plurality of flat wires or circular wires. The shaft of the transporter catheter may comprise plurality of segments of varying hardness characteristics. The hardness of the first segment of the shaft of the transporter catheter located between the first balloon and the second balloon may be less than the hardness of the second segment of the shaft between the second balloon and the proximal end of the catheter. In another embodiment, the hardness of a part of the first segment of the shaft proximate to the orienting balloon may be less than the hardness of a part of the first segment of the shaft proximate to the anchor balloon.

Another embodiment of the invention provides devices, systems, and methods that comprise an introducer catheter that has a capability to maneuver through the vasculature of a patient's body independently from the transporter catheter. Such introducer catheters are generally known as "steerable guide" catheters and comprise at least a first handle assembly comprising a first deflecting mechanism coupled to a distal end region of the steerable guide catheter to apply a deflecting force to bend the distal end region, the first deflecting mechanism adapted to bend the distal end region in a first articulated position, and a second deflecting mechanism coupled to the distal end region of the steerable guide catheter to apply a deflecting force to bend the distal end region, the second deflecting mechanism adapted to bend the distal end region in a second articulated position. The steerable guide catheter further comprises at least an open interior lumen to accommodate passage of a transporter catheter to assist in the orientation and positioning of the steerable catheter. The transporter catheter located inside the steerable guide catheter assists in orienting and positioning the steerable catheter and compliments the functioning of the deflecting mechanisms to advance the steerable catheter smoothly. After the steerable guide catheter is positioned at the desired location, the orienting balloon and the anchor balloon in the transporter catheter are deflated and the transporter catheter is removed from the interior lumen of the steerable guide catheter.

DETAILED DESCRIPTION OF THE INVENTION

Embodiments of the present invention are described below in detail with reference to the accompanying drawings. Systems using transporter catheters according to the present invention exhibit improved maneuverability, flexibility, and kink resistance.

Figure 1:
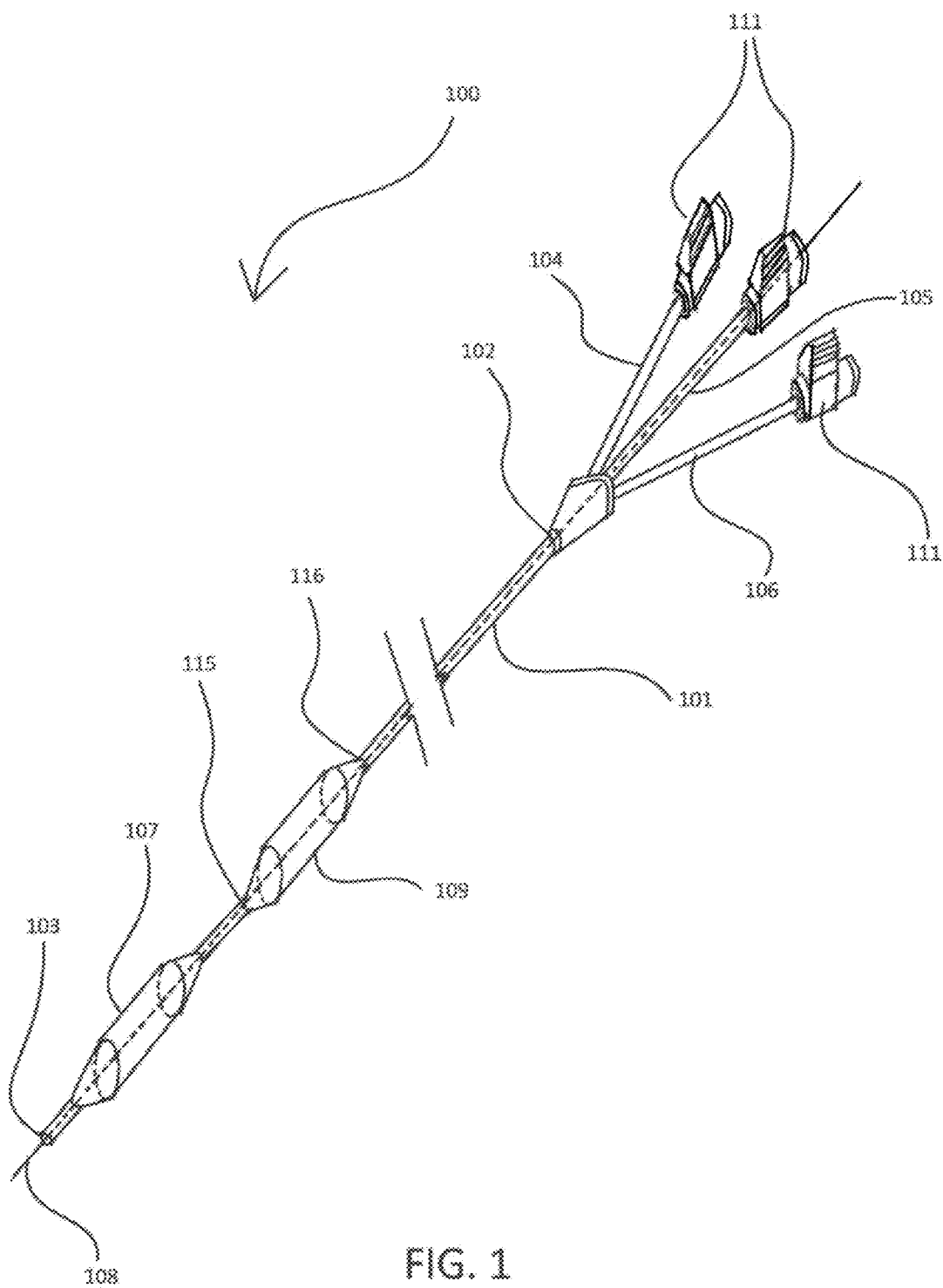
FIG. 1 is a perspective view of a transporter catheter in accordance with one embodiment of the present invention.

In reference to FIG. 1, catheter 100, comprises a shaft 101, having a proximal end 102, and a distal end 103, and a first lumen 104, a second lumen 105, and a third lumen 106. First lumen 104 extends the entire length of said shaft 101 and communicates with an orienting balloon 107 located at distal end 103 of said shaft 101. Second lumen 105 extends the entire length of said shaft 101, and allows for the placement of catheter 100 over guidewire 108. Third lumen 106 communicates with an anchor balloon 109, which is located between the orienting balloon 107 and the proximal end 102 of the shaft 101. In one embodiment, the anchor balloon is located proximal to the orienting balloon.

In another embodiment, the third lumen 106 communicating with the anchor balloon may be adapted to receive a removable stiffening stylet to ease insertion by stiffening up the catheter shaft. In yet another embodiment, two removable stiffening stylets may be inserted, one inserted in lumen 104 and another inserted in lumen 106. Stiffening stylet(s) are inserted to extend substantially the entire length of member 101 until just proximal to anchor balloon 109. If two stylets are used, the practitioner may insert one stylet further than the other to adjust the amount of stiffness as needed. In one embodiment, a stylet is not inserted beyond the anchor balloon.

Lumens 104, 105 and 106 are attached to Luer connectors 111 at their proximal end. Said Luer connectors are then connected to syringes, valves etc. to provide for the introduction of balloon inflation media. In another embodiment, a radiopaque marker may be located on the orienting balloon 107. In yet another embodiment, a radiopaque marker may be located along shaft 101, including distal end 103. In another embodiment, a radiopaque marker may be located on the anchor balloon 109. In one embodiment, an imaging marker is fixed to shaft 101 at its distal end portion (disposed slightly proximal from the tip and in the area proximate to a front-end portion of the orienting balloon 107). In another embodiment, the imaging marker is fixed on the orienting balloon 107. In yet another embodiment, the imaging marker is fixed on the anchor balloon 109. In one embodiment, the imaging marker is formed from a radiopaque material (for example, gold, platinum, tungsten or alloys of these metals or from a silver-palladium alloy, or a platinum-iridium alloy). By so doing, it is possible to confirm the location and then advance the catheter 100 through a patient's vasculature by means of radiographic imaging and visualization. In one embodiment, the shaft of the transporter catheter may have a lumen from its proximal end to its distal end to infuse medication at the distal end by using a luer connector at the proximal end.

The mechanical properties of segments of shaft 101 can be varied by adjusting and varying the properties of the cylindrical braid structure(s) and the polymeric materials (e.g., dimension of the cylindrical braid structure and/or durometers of the polymers). Additionally, the mechanical properties of the segments of shaft 101 can be varied along the length of the shaft 101 in accordance with certain embodiments of the disclosure or can be substantially uniform along the entire length of the shaft 101 in accordance with other embodiments of the disclosure.

Figure 2:
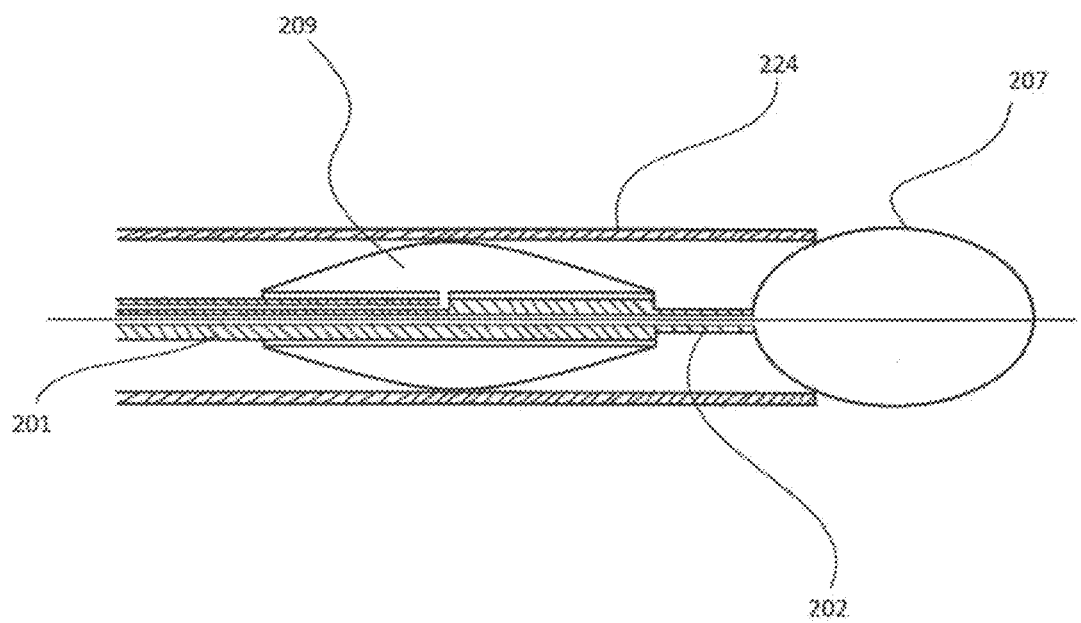
FIG. 2 is a perspective view of a transporter catheter having a first segment of the transporter catheter that is more flexible than a second segment of the transporter catheter.

In one embodiment, the shaft 101 may be provided with a rigidity-imparting body. In one embodiment, the rigidity-imparting body is provided using a blade. The blade may be formed of a metal wire or a synthetic resin wire. In another embodiment, the rigidity-imparting body is provided to the shaft over the entire length 201 of the shaft except for the distal end portion 202 of the shaft from the anchor balloon 209 to the orienting balloon 207, as shown in FIG. 2. The anchor balloon 209 anchors the rigidity-imparted body 201 to the inner surface of a lumen of the introducer catheter 224. In another embodiment, the rigidity-imparting body is provided to the shaft 101 in a range from the proximal end 102 of the transporter catheter to the distal end 115 of the anchor balloon 109.

Figure 3:
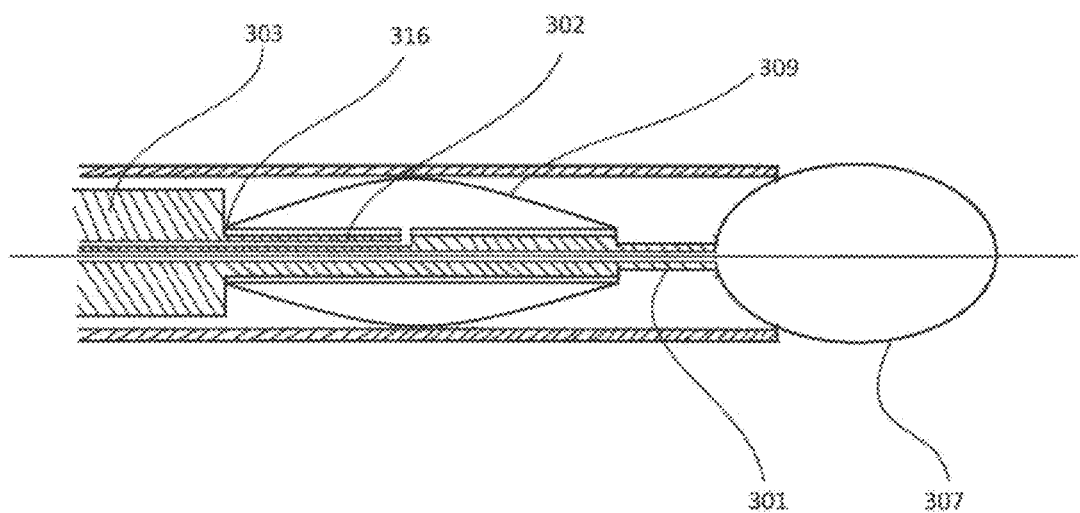
FIG. 3 is a perspective view of a transporter catheter having multiple segments of the transporter catheter with multiple degrees of flexibility.
Figure 4A:
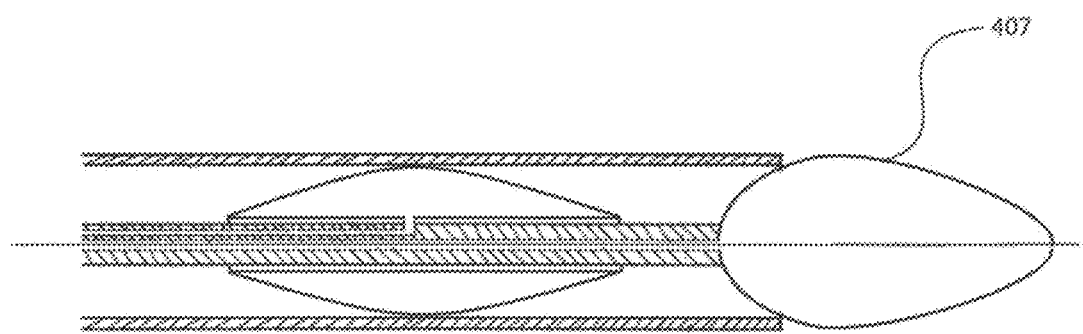
FIG. 4a is a perspective view of a transporter catheter showing a contoured orienting balloon that facilitates smooth movement of the orienting balloon by reducing drag.
Figure 4B:
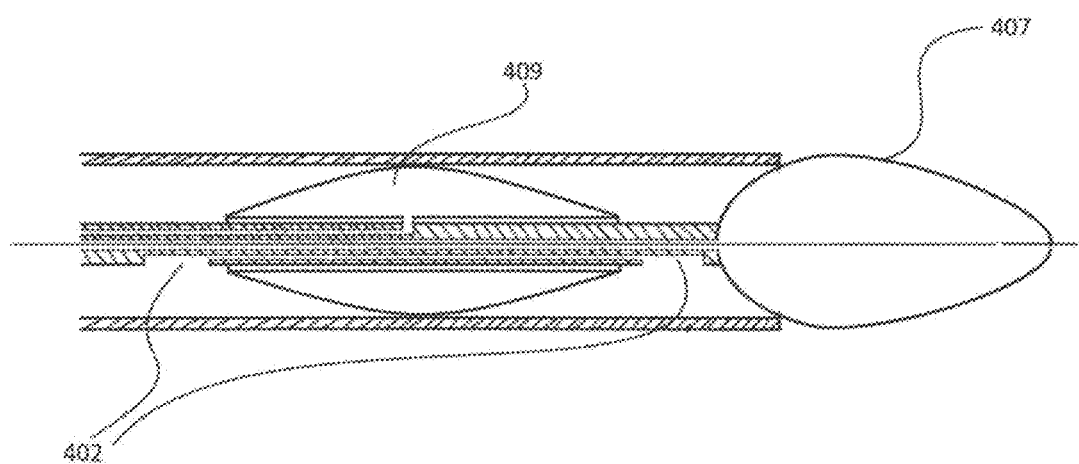
FIG. 4b is a perspective view of a transporter catheter showing a perfusion lumen to perfuse blood across the anchor balloon when the anchor balloon is inflated.
Figure 4C:
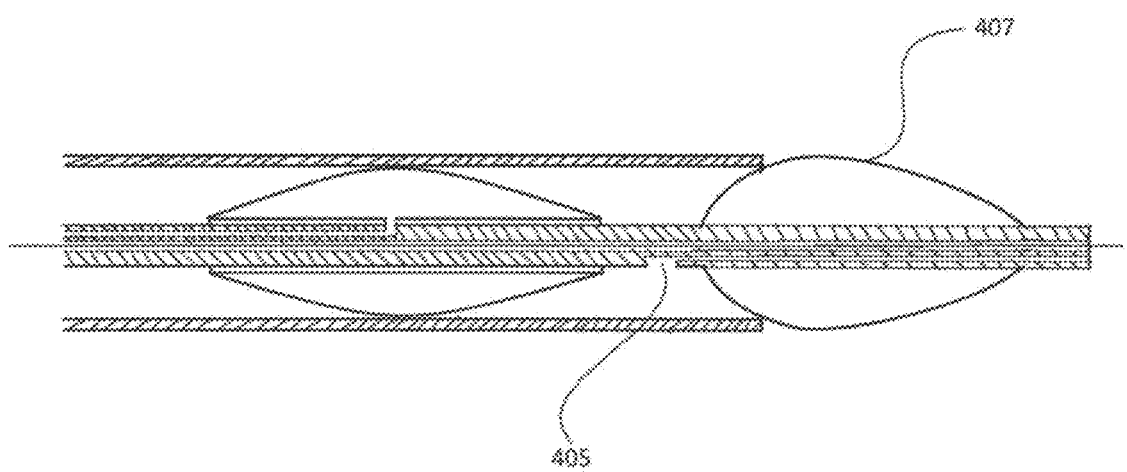
FIG. 4c is a perspective view of a transporter catheter showing a perfusion lumen to perfuse blood across the orienting balloon when the orienting balloon is inflated.
Figure 5:
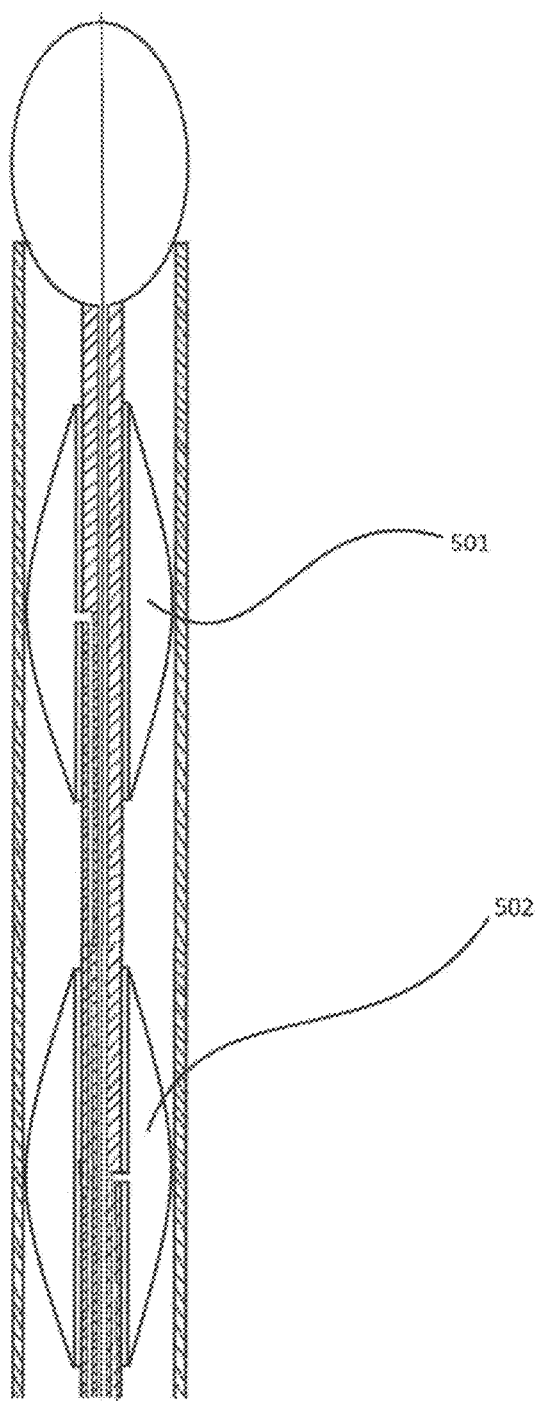
FIG. 5 is a perspective view of a transporter catheter with more than one anchor balloons.
Figure 6:
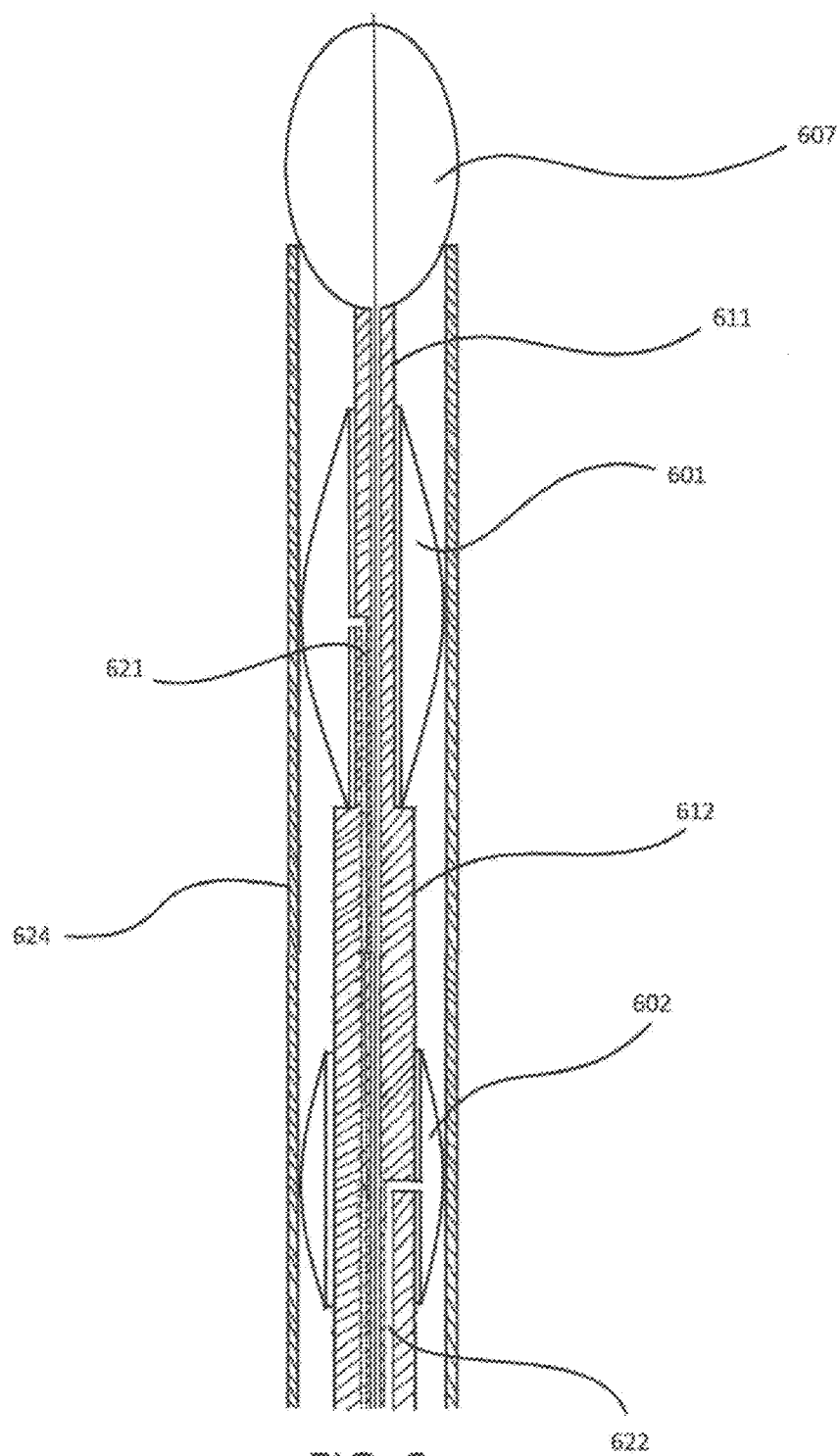
FIG. 6 is a perspective view of a transporter catheter having multiple segments of varying degrees of hardness, with an anchor balloon present on more than one segment.

In another embodiment of the invention shown in FIG. 3, the shaft has a first flexible region 301 disposed at the distal end of the shaft, a second flexible region 302, which is continuous with the first flexible region 301 and flexible, but has a higher degree of hardness than the first flexible region 301, and a flexible region 303, which is continuous with the second flexible region 302 and has a higher degree of hardness than the second flexible region 302. In the embodiment shown in FIG. 3, the most flexible first flexible region 301 is between the orienting balloon 307 and the anchor balloon 309. The second flexible region 302 of the shaft is substantially covered by the anchor balloon 309. The third flexible region 303 has a degree of hardness higher than the hardness of the second and the first flexible region and extends from the proximal end 102 of the catheter 100 to the proximal edge 116, 316 of the anchor balloon. The flexibility of transporter catheter becomes stepwise lower from its distal end to its proximal end. Because the portion 301 of the shaft proximate to the orienting balloon 307 is flexible, the orienting balloon 307 is capable of passing through a curved portion of a vessel with relative ease. In one embodiment as illustrated in FIG. 4a, the distal end of the orienting balloon 407 is contoured to provide smooth movement of the orienting balloon. In another embodiment, the surface of the orienting balloon is coated with a drag-reduction coating. In another embodiment, the surface of the orienting balloon may have a wavy contour (not shown) when inflated to provide channels for perfusion of blood across the orienting balloon when the orienting balloon is inflated. In one embodiment as illustrated in FIG. 4b, a perfusion lumen 402 is provided to perfuse blood across the anchor balloon 409 when the anchor balloon 409 is inflated. In another embodiment as illustrated in FIG. 4c, a perfusion lumen 405 is provided to perfuse blood across the orienting balloon 407 when the orienting balloon 407 is inflated. In one embodiment as illustrated in FIG. 5 multiple anchor balloons 501, 502 may be present. In another embodiment illustrated in FIG. 6, at least one anchor balloon may be present in each flexible region of the shaft, e.g., a first anchor balloon 601 is present in a first flexible region 611 and a second anchor balloon 602 is present in a second flexible region 612. The first anchor balloon 601 is inflated using the first lumen 621 and the second anchor balloon 602 is inflated using the second lumen 622, thereby the first anchor balloon 601 may be inflated or deflated independent of the inflation or deflation of the second anchor balloon 602, and vice versa. In another embodiment (not shown), a single lumen connects a plurality of anchor balloon whereby all anchor balloons inflate or deflate together. In one embodiment, one or more anchor balloons may be anchored to the introducer catheter 624 depending on how the orienting balloon 607 advances through the vasculature of a patient's body. More than one anchor balloon may be inflated independently, if the orienting balloon experiences increased resistance.

Figure 7:
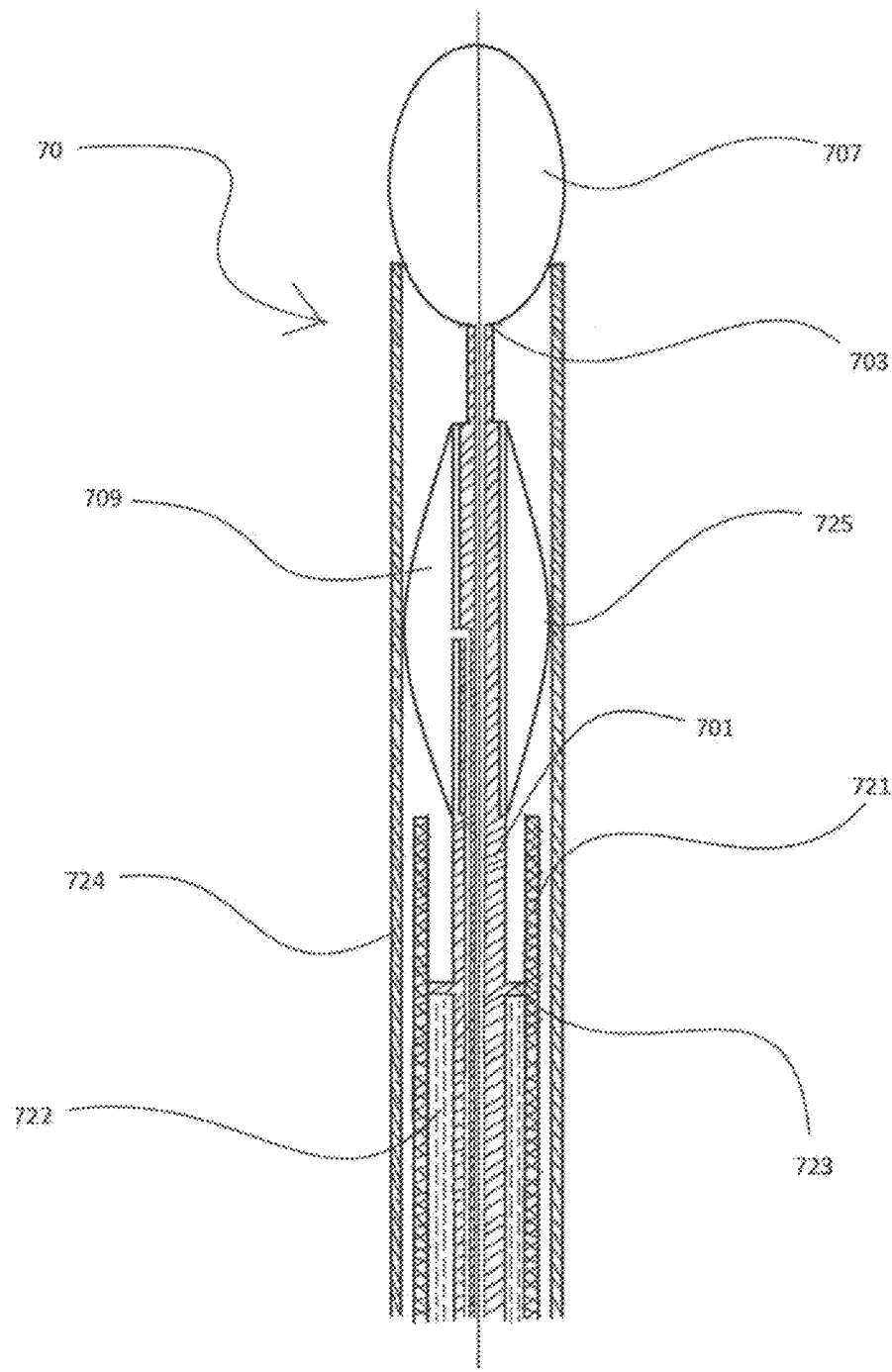
FIG. 7 is a perspective view of a transporter catheter having a hydraulic system to advance the transporter catheter.

In yet another embodiment of the invention shown in FIG. 7, an introducer catheter to which a transporter catheter is anchored is advanced using hydraulic pressure. The system 70 comprises the transporter catheter with a shaft 701, an orienting balloon 707 located at a distal end of the shaft 701, a hydraulic fluid lumen 721, hydraulic fluid 722, and a piston 723 movably disposed in the hydraulic fluid lumen and connected to the shaft 701 of the transporter catheter. The piston forms a seal with an interior surface of the hydraulic fluid lumen. A hydraulic driver, e.g., a syringe that generates hydraulic pressure against the piston sufficient to advance the shaft 701 of the transporter catheter is used. The anchor balloon 709, which is connected to the shaft 701 advances with the shaft. Upon inflation, the anchor balloon 709 is anchored to the inner surface 725 of the introducer catheter 724, and thereby the advancement of the anchor balloon 709 also advances the introducer catheter 724 through a patient's vasculature. In one embodiment, the method of advancing the introducer catheter a first distance inside a patient's vasculature comprises the following steps: (a) positioning the transporter catheter inside the introducer catheter; (b) inflating the orienting balloon; (c) adjusting the position of the transporter catheter whereby the orienting balloon is substantially outside the distal end of the introducer catheter; (d) inflating the anchor balloon to anchor the transporter catheter to the inside surface of the lumen of the introducer catheter; (e) applying hydraulic pressure to the piston to advance the introducer catheter. In another embodiment, after advancing the introducer catheter a first distance using hydraulic pressure, the introducer catheter is advanced a second distance using the following method: (i) deflating the anchor balloon, (ii) reducing the hydraulic pressure, (iii) repositioning the transporter catheter inside the lumen of the introducer catheter, (iv) inflating the anchor balloon to anchor the transporter catheter to the introducer catheter and (v) applying hydraulic pressure again. Steps (i) to (v) may be repeated to continue advancing the catheter system. A standard inflation medium is a 1:2 mixture of contrast medium and normal saline solution.

In one embodiment, the length of the transporter catheter 100 may be from about 100 cm to about 250 cm. The end use and the length of the introducer catheter may determine the length of the transporter catheter. By way of illustration only and not by way of limitation, and depending on physiology of a patient, a cerebral vasculature application may warrant a catheter length from about 100 to about 150 cm; a coronary vasculature application may warrant a catheter length from about 100 to about 160 cm in length; a peripheral vasculature application may warrant a catheter length from about 70 to about 100 cm in length; a renal vasculature application may warrant a catheter length from about 60 to about 90 cm in length; and a hepatic vasculature application may warrant a catheter from about 70 to about 100 cm in length. The outer diameter of the shaft 101 of the transporter catheter 100 may range from about 2 French to about 12 French or higher. However, the dimensions of the shaft 101 of transporter catheter 100 may vary in accordance with various applications of the catheter system and size of the introducer catheter. In one embodiment, the outer diameter of the orienting balloon is about the same as the outer diameter of the introducer catheter. In another embodiment, the outer diameter of the orienting balloon is greater than the outer diameter of the introducer catheter.

The distal end 103 of the shaft 101 may or may not be tapered. In one embodiment, shaft 101 may have a taper, with the proximal end 102 having larger diameter than the distal end 103. The end use and the inside diameter of the introducer catheter may determine the outer diameter of the shaft 101. Shaft 101's inner diameter may range from about 1 French to about 3 French. If shaft 101 is to receive a guidewire 108, it will need to be proportioned accordingly. In one embodiment, guidewires up to 1.4 French in diameter may be used. In another embodiment, guidewires may not be used in conjunction with the transporter catheter and the transporter catheter may not have lumen 105 for a guide wire. In one embodiment, the transporter catheter may deliver the introducer catheter to the desired location over a guidewire. In another embodiment, the transporter catheter may deliver the introducer catheter to the desire location without the use of the guidewire. After the introducer catheter is positioned, the stylet(s) if present may be removed, then the orienting balloon and the anchor balloon are deflated by means of a hand held syringe or other means.

Figure 8A:
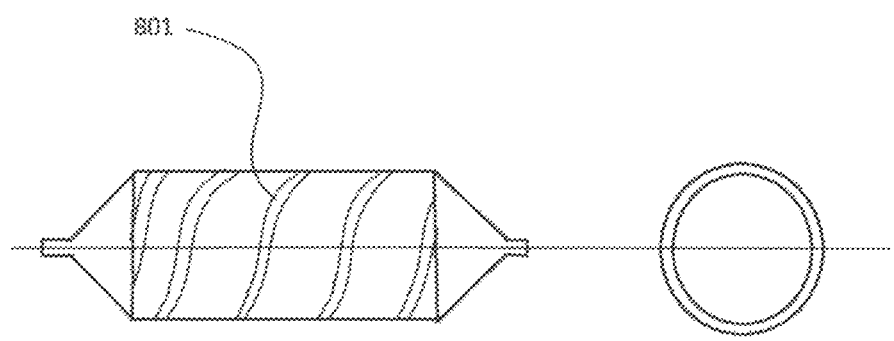
FIG. 8a-d are perspective views of modifications to the surface of the anchor balloon to enhance anchoring to the inner surface of an introducer catheter.
Figure 8B:
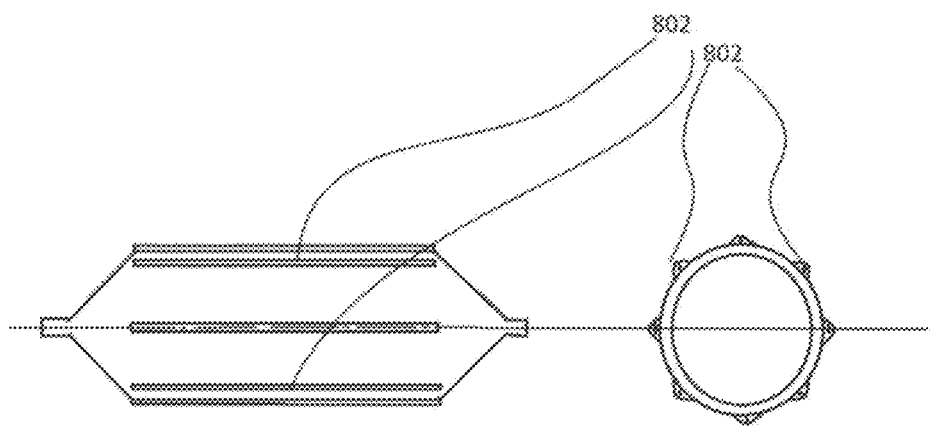
Figure 8C:
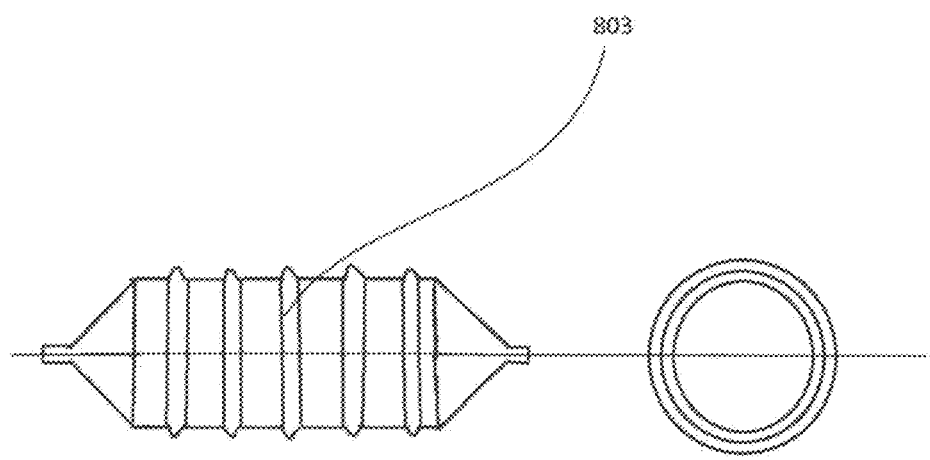
Figure 8D:
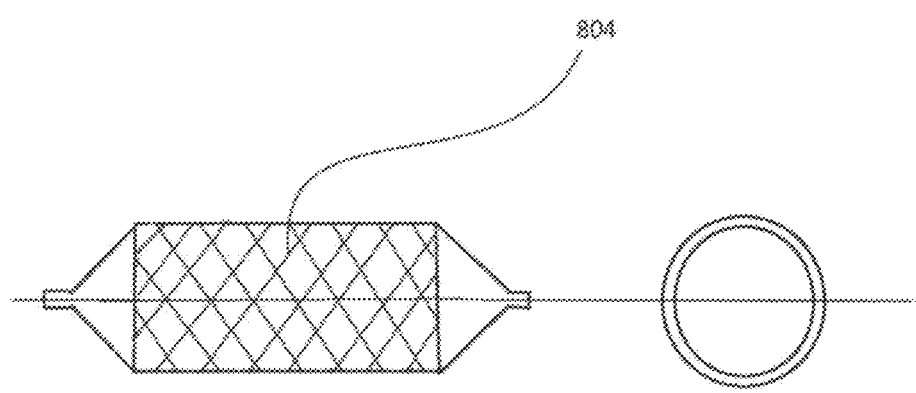

The material for shaft 101, lumens 104, 105 and 106, and orienting balloon 107 may contain any one or more of the following additives. By way of illustration only and not limitation, mention may be made of radiopaque fillers, slip additives, and hydrophilic coatings. In one embodiment, silicon provides hydrophilic coating. In another embodiment, the anchor balloon may be made of materials and/or coated with materials that provide frictional resistance to reduce slippage. Examples of such materials include polyurethane. In another embodiment, the anchor balloon may have serrations 801 as illustrated in FIG. 8*a* and/or raised projections 802 as illustrated in FIG. 8*b* to enhance the anchoring capability of the anchor balloon to the inside of the introducer sheath after the anchor balloon is inflated. The serrations and/or raised projections may have spiral shape 801 as shown in FIG. 8*a*, linear shape 802 as shown in FIG. 8*b*, and other shapes, see for example, circular ring shape 803 (see FIG. 8*c*) and crisscross checkered shape 804 (see FIG. 8*d*). The projections may have inserts, e.g., wires. The wires or wire segments may be made of various materials, and may each be made of the same materials or materials with similar material properties, or different materials having different properties. As an example, such wires or wire segments may be formed of stainless steel. The material of wires may be stiffer than the materials forming the wall of the balloon. The projections enhance the anchoring capability of the anchor balloon to the inside surface of the outer catheter, such as an introducer catheter, by coarsening the outer surface of the anchor balloon and anchoring the outer surface of the anchor balloon to the inner surface of the introducer catheter. The wire or wire segments forming the projections may also have any cross-sectional geometric shape, including for example, circular, square, or triangular, and different projections may have different cross-sectional shapes. Rounded shapes and/or smooth edges would help to prevent the wire or wire segment forming the projection from perforating the wall of the anchor balloon. In one embodiment, the wire or wire segments may be hollow to allow for passage of blood, thereby preventing occlusion of blood when the anchor balloon is inflated.

In one embodiment, the wires or wire segments comprise a material that is radiopaque (either a homogeneous material or a material that is non-radiopaque and provided with a radiopaque coating), and thus visible under fluoroscopy. Making the projections visible may also allow the clinician to better understand the location and orientation of the anchor balloon, as well as the position of the anchor balloon before inflating and anchoring the balloon to the inside surface of the introducer catheter.

Figure 9:
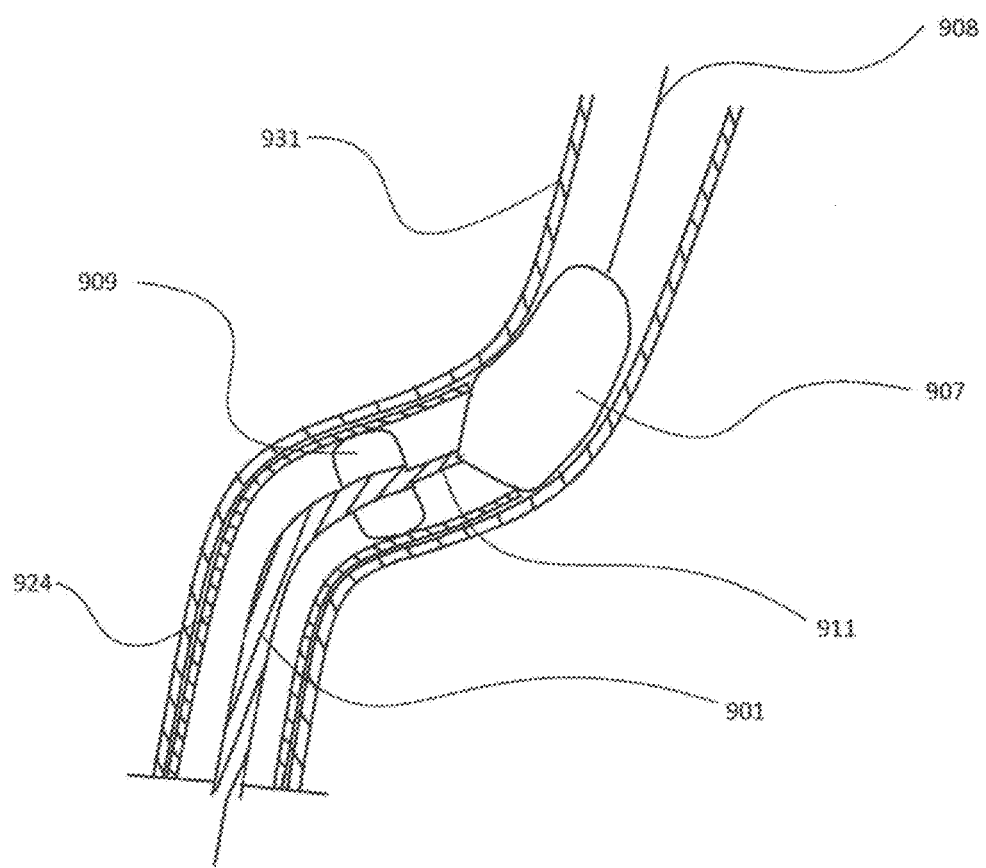
FIG. 9 is a perspective view of a catheter system comprising a transporter catheter and an introducer catheter advancing through a vasculature of a patient's body.

In operation as illustrated in FIG. 9, the orienting balloon 907 orients and maneuvers the catheter system comprising the introducer catheter 924 and the transporter catheter 901 through the curves of the vasculature 911 in a patient's body. The orienting balloon 907 protrudes outside the introducer catheter 924. In one embodiment, about 50% of the orienting balloon protrudes outside the introducer catheter 924. In another embodiment, more than 50% of the orienting balloon 907 protrudes outside the introducer catheter. In yet another embodiment, about 80% of the orienting balloon 907 protrudes outside the introducer catheter 924. In another embodiment, less than 50% of the orienting balloon 907 protrudes outside the introducer catheter 924. In one embodiment, the orienting balloon may be inflated using a pressure from about 2 atmospheres to about 10 atmospheres or higher. In another embodiment, the orienting balloon, is inflated using a pressure of about 4 atmospheres. The anchor balloon 909 anchors the shaft of the transporter catheter 901 to the inner surface of the lumen of the introducer catheter 924. In one embodiment, a guide wire 908 may be present. In another embodiment, segment 911 between the anchor balloon 909 and the orienting balloon 907 may be more flexible than segment 901 of the transporter catheter. The catheter system may be advanced by pushing and/or torqueing the introducer catheter 924, or the transporter catheter 901, or both. If the catheter system is advanced by pushing the introducer catheter, the wall of the introducer catheter should have enough axial strength to be pushed through the patient's vasculature via a force applied at its proximal end ("pushability"). It is also desirable for the introducer catheter to be capable of transmiting a torque applied at the proximal end along the length of the shaft through to the distal end ("torqueability"). An introducer catheter should also have enough flexibility to conform substantially to the patient's vasculature and yet resist kinking as it is pushed and/or torqued through the patient's vasculature and conforms to the patient's vasculature. The wall of an introducer catheter 924 that is advanced by pushing the introducer catheter is thick, and increasing the bore size of an introducer catheter having a given overall diameter requires utilizing a thinner wall. Now that catheters are used in smaller and smaller passages, there is a growing need to use introducer catheters that have a smaller outer dimension. However, a thin-walled introducer catheter that is pushed through the patient's vasculature is more likely to collapse upon itself or kink when a push force and/or torque is applied at its proximal end. On the other hand, if the introducer catheter 924 is pulled through the patient's vasculature by an anchor balloon 909 of a transporter catheter, then the wall of the introducer catheter 924 may be relatively thinner.

Figure 10A:
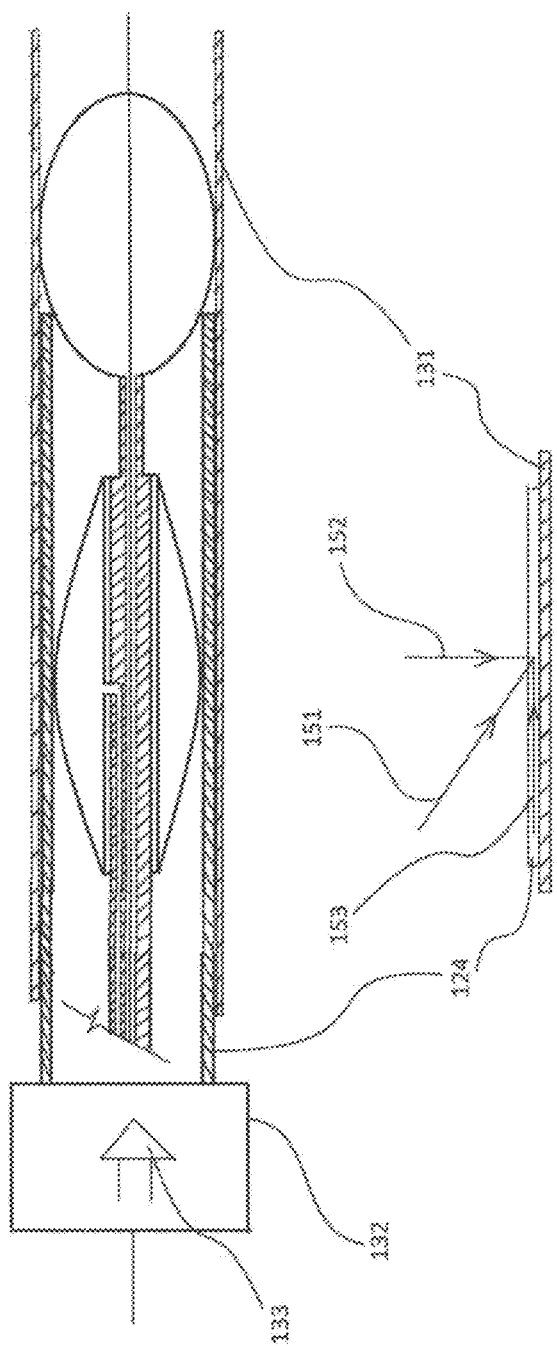
FIG. 10a-b is a schematic of forces acting on a wall of an introducer catheter when it is pushed at its proximal end or pulled at its distal end.

FIG. 10*a* is a schematic of the forces that act on the introducer catheter when a user pushes the introducer catheter in direction 133 at the proximal end of the introducer catheter 124 using a handle 132. The push force 151 on the wall of the introducer catheter has a horizontal component 153 that advances the introducer catheter 124 through the vasculature 131 of the patient's body, and a vertical component 152 that presses on the wall of the introducer catheter 124 against the wall of the vasculature 131. Because component 152 is directed towards the wall of the vasculature 131, the component 152 adds frictional resistance and drag to the introducer catheter as it advances through the vasculature. Because of the additional frictional resistance, a greater push force is required, thereby requiring a thicker wall so that the introducer catheter does not collapse or kink. A greater push force also results in additional frictional resistance because of a larger vertical component 152. Total frictional resistance depends on the contact area between the introducer catheter and the vasculature and therefore depends in part on the length of the introducer catheter that is inserted into the vasculature of a patient's body. Because of the compounding of the frictional resistance with increase in push force, the length to which an introducer catheter can be pushed inside the vasculature may be limited.

Figure 10B:
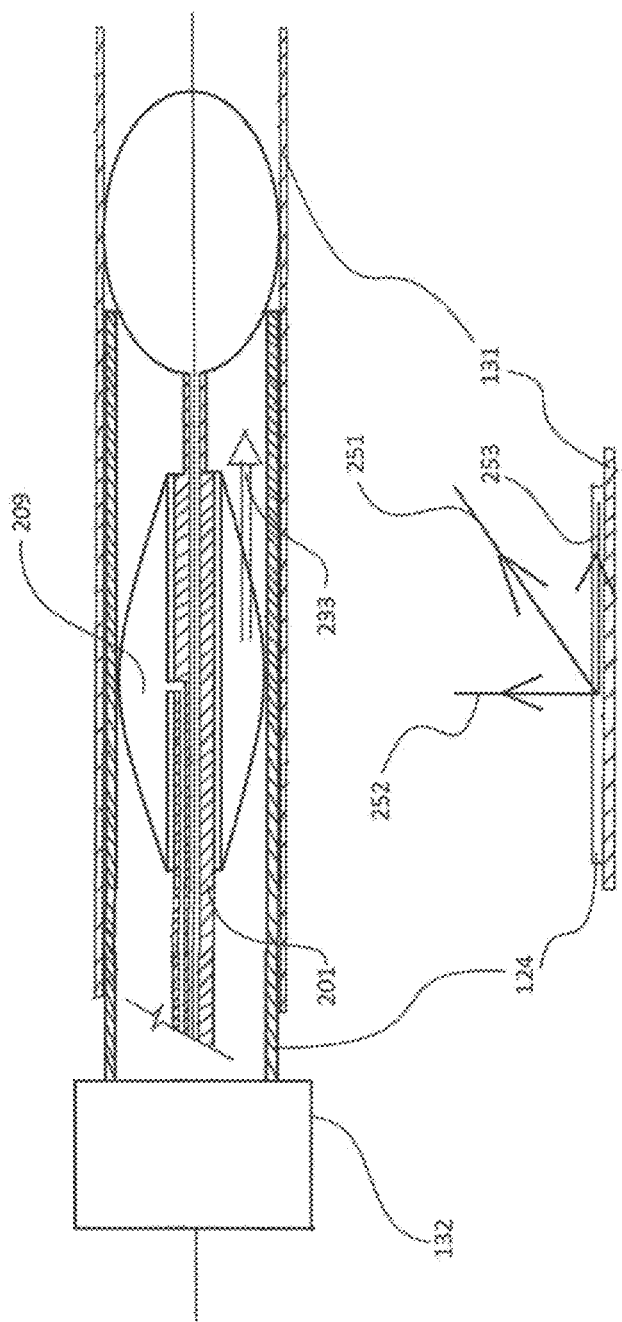

FIG. 10*b* is a schematic of the forces that act on the introducer catheter as it is pulled by the anchor balloon of the transporter catheter when the user pushes the transporter catheter to advance the introducer catheter. When a user pushes the transporter catheter 201 and with it, its anchor balloon 209 in the direction 233, the anchor balloon exerts a pull force 251 on the wall of the introducer catheter 124. The pull force 251 on the wall of the introducer catheter has a horizontal component 253 that advances the introducer catheter 124 through the vasculature 131 of the patient's body, and a vertical component 252 that pulls the wall of the introducer catheter 124 away from the wall of the vasculature 131. Because component 252 is directed away from the wall of the vasculature, the component 252 reduces the frictional resistance and the drag on the introducer catheter as it advances through the vasculature. Consequently, a smaller push force is required on the transporter catheter to advance the catheter system through the vasculature. Furthermore, because the walls of the introducer catheter experience a pull force at the distal end rather than a push force at the proximal end, the possibility of kinking the wall of the introducer catheter is reduced, and a thinner wall may be used for the introducer catheter. The transporter catheter is removed after the introducer catheter is positioned at a desired location. Thus, for a given outer diameter of an introducer catheter and by using a transporter catheter to advance the introducer catheter (or to advance any other outer catheter such as a sheath, a guide catheter, or a mother catheter), the user may use an introducer catheter with a thinner wall, thereby providing a larger diameter of its inner lumen.

Figure 11:
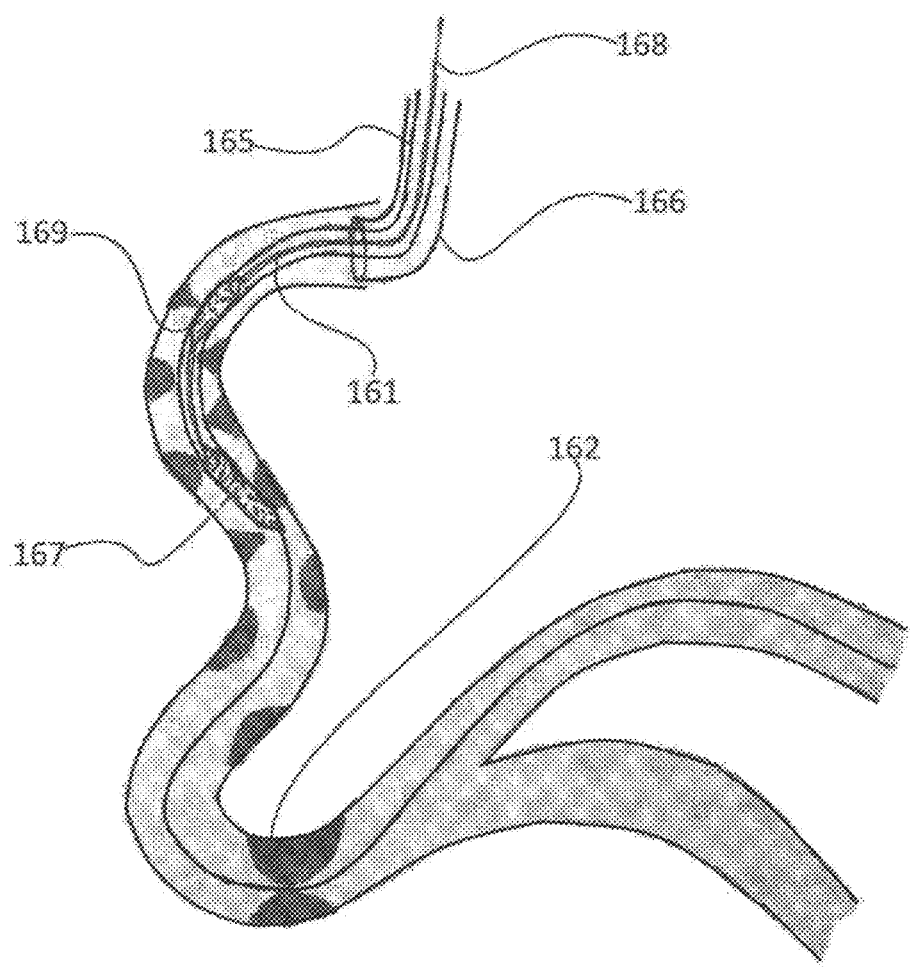
FIG. 11 is a perspective view of a catheter system comprising a mother catheter, an inner support catheter and a transporter catheter advancing through an adverse arterial lumen.
Figure 12:
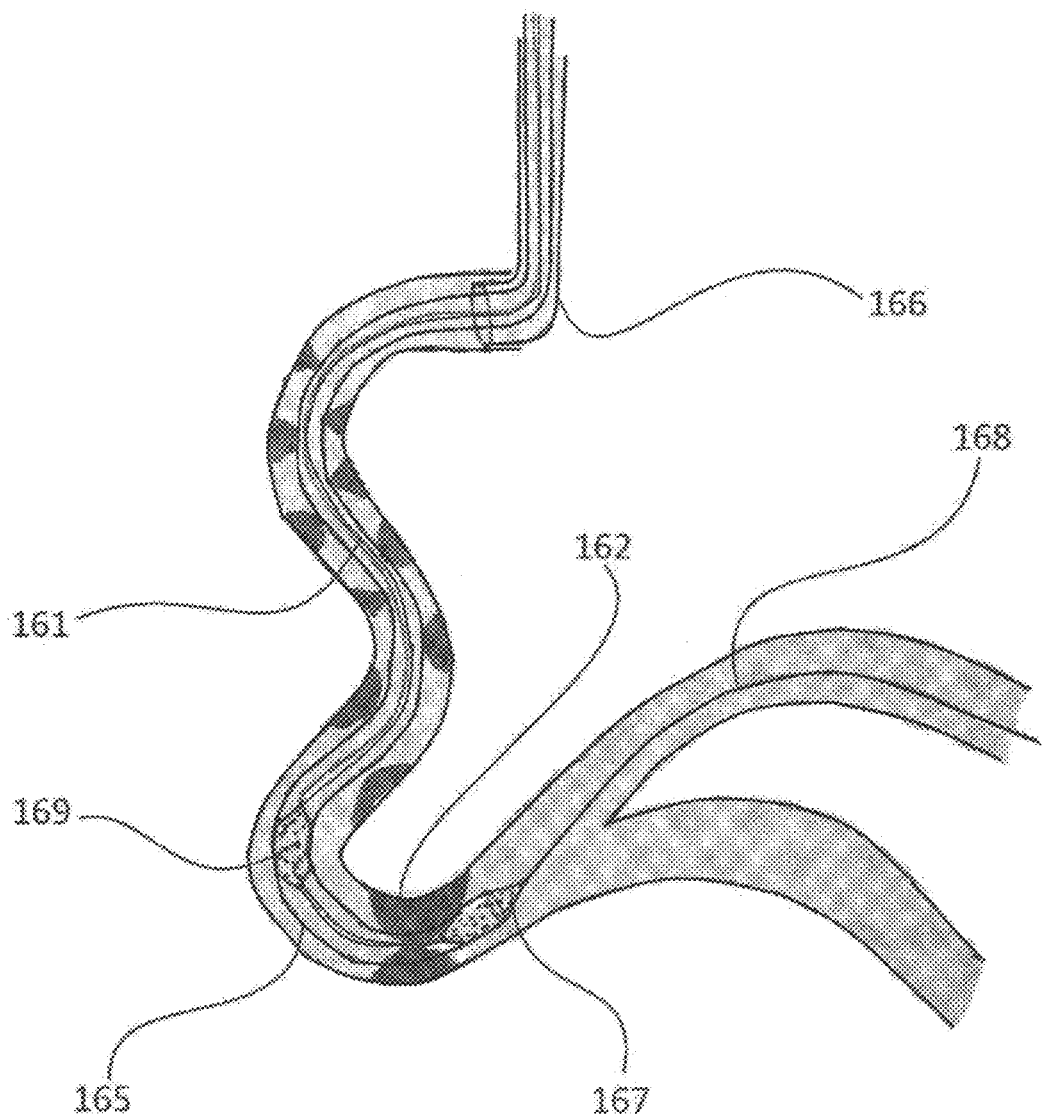
FIG. 12 is a perspective view of a catheter system comprising a mother catheter, an inner support catheter and a transporter catheter advanced through an adverse arterial lumen.
Figure 13:
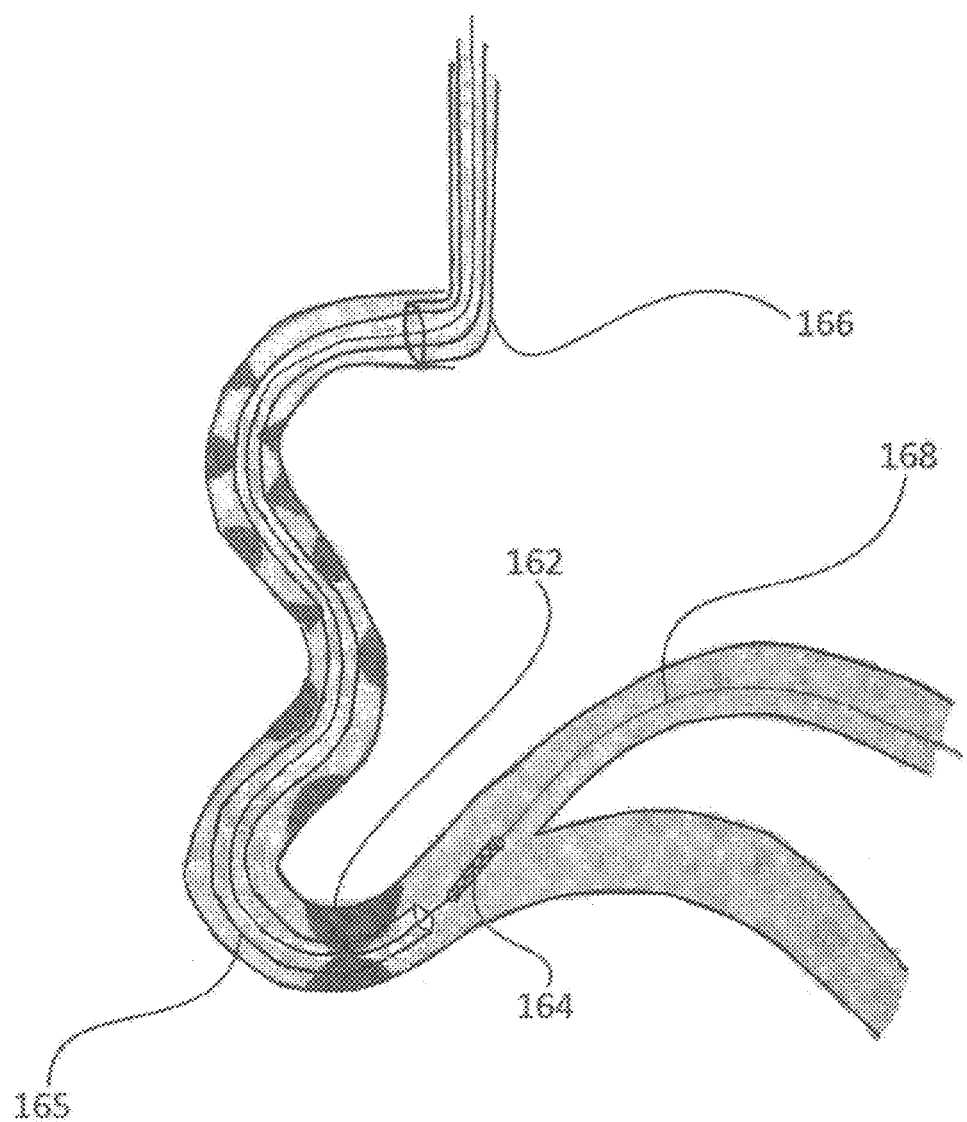
FIG. 13 is a perspective view of positioning of a stent in an adverse arterial lumen using a catheter system comprising a mother catheter, an inner support catheter and a transporter catheter.

In another embodiment (see FIGS. 11 and 12) comprising a mother catheter 166 and an inner support catheter (daughter or child catheter) 165 advanced on a guide wire 168, the inner support catheter 165 is advanced by placing a transporter catheter 161 inside a lumen of the inner support catheter 165, with the transporter catheter having an orienting balloon 167 protruding from the tip of the inner support catheter and another balloon 169, which is inside the lumen of the inner catheter 165 providing anchoring. Using this multi-balloon transporter catheter 161 to advance the inner catheter 165, the double balloon catheter composite is advanced through an adverse arterial lumen, beyond the stenosis 162. After the inner support catheter has been successfully placed beyond the stenosis 162, the transporter catheter is withdrawn after deflating the orienting and the anchor balloons. Then a stent 164 (see FIG. 13) or other hardware may be placed through the inner support catheter 165 distal to the stenosis 162. Subsequently the inner support catheter is withdrawn and the stent 164 is then positioned usually by pulling the stent 164 to the site of interest and deploying the stent 164 (FIG. 13). In one embodiment, at least one hole may be provided in the body of the inner support catheter to provide for perfusion of blood from outside the inner support catheter into the inner support catheter.

The inner support catheter can be made with hydrophilic coating to minimize friction between the arterial lumen and the external surface of the inner support catheter. The wall of the inner support catheter can be made thinner whereby the diameter of the inner lumen of the support catheter is larger and the outer dimensions of the inner support catheter conforms to the geometry of the coronary artery. Because the multi-balloon transporter catheter is used to advance the inner support catheter, the inner support catheter does not require as much structure (such as larger wall thickness) to transmit longitudinal axial forces.

In one embodiment, the transporter catheter 100 is manufactured via an extrusion process. Given that extrusion processes are well known in the art, the general process is not discussed in detail herein. In general, the extrusion process begins by heating the polymer until melted. The melted polymer is then forced under pressure through an extrusion tip and die. As the melted polymer exits the extrusion tip and die, it is cooled. A typical cooling method employs a water bath. The cooling step solidifies the device with the desired dimensions.

Shaft 101 and lumens 104, 105 and 106 may be manufactured using any commercially available catheter materials. Materials include, without limitation, polyethylene, polyamide, urethane. It is also possible to use polyolefin such as polypropylene; polyester such as polyamide and polyethylene terephthalate; fluorine-based polymer such as PTFE (polytetrafluoroethylene); PEEK (polyether ether ketone); polyimide; synthetic resin elastomer such as olefinic elastomer (for example, a polyethylene elastomer and a polypropylene elastomer), polyamide elastomer, styrenic elastomer (for example, a styrene-butadiene-styrene copolymer, a styrene-isoprene-styrene copolymer, a styrene-ethylene butylene-styrene copolymer); polyurethane, urethane-based elastomer, and fluorine-based elastomer; synthetic rubber such as urethane rubber, silicone rubber, and butadiene rubber. The specific material chosen will depend on the end use of the catheter, the size of the vessel to be accessed, and whether or not a stylet or stylets will be used to assist during insertion and advancement. In other words, the desired end use will dictate the degree of stiffness, flexibility, strength and slipperiness of the material. Orienting balloon 107 and anchor balloon 108, may be manufactured using any commercially available balloon materials. Materials include, without limitation, latex, silicone, ethylvinylacetate, and urethane.

It will be appreciated that several of the above-disclosed and other features and functions, or alternatives or varieties thereof, may be desirably combined into many other different systems or applications. Also, it will be appreciated that various alternatives, derivatives, modifications, variations or improvements thereof or therein may be subsequently made by those skilled in the art, which are also intended to be encompassed by the following claims.

In the description above, for the purposes of explanation, numerous requirements and certain details have been included in order to provide an understanding of the embodiments. It will be apparent however, to one skilled in the art, that one or more other embodiments may be practiced without some of the details. The particular embodiments described are not provided to limit the invention, but merely to illustrate it. The scope of the invention is not to be determined by the specific examples provided above. In other instances, well-known structures, devices, and operations have been shown in block diagram form or without detail in order to avoid obscuring the understanding of the description. Where appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in fewer than all features of a single disclosed embodiment. In another situation, an inventive aspect may include a combination of embodiments described herein or in a combination of fewer than all aspects described in a combination of embodiments.

The invention claimed is:

1. A catheter system comprising: an outer catheter comprising at least one lumen; a transporter catheter located in the at least one lumen of the outer catheter, the transporter catheter comprising a shaft; a first balloon formed on the shaft and positioned adjacent to a distal end of the shaft; at least a second balloon formed on the shaft and located between the first balloon and a proximal end of the shaft, the at least second balloon upon inflation pressing against an inner surface of the at least one lumen of the outer catheter thereby anchoring the transporter catheter to the outer catheter; and wherein the transporter catheter is configured to be pushed to advance the outer catheter within a patient's vasculature with both the first balloon and the at least second balloon fully inflated and at least a portion of an outer surface of the outer catheter slidably engaged to an inner surface of the patient's vasculature.

2. The catheter system of claim 1, wherein the shaft comprises at least one stiffening stylet for stiffening the shaft.

3. The catheter system of claim 1, wherein the shaft comprises a lumen to receive a guidewire.

4. The catheter system of claim 1, further comprising at least one imaging marker.

5. The catheter system of claim 1, wherein the shaft is tapered and the proximal end of the shaft has a diameter greater than a diameter of the distal end of the shaft.

6. The catheter system of claim 1, wherein the shaft comprises a plurality of segments having varying degrees of hardness.

7. The catheter system of claim 6, wherein a degree of hardness of the varying degrees of hardness of a segment of the shaft located between the first balloon and the at least second balloon is different from the degree of hardness of the varying degrees of hardness of a segment of the shaft located between the at least second balloon and the proximal end of the shaft.

8. A catheter system comprising:
an outer catheter comprising at least one lumen;
a transporter catheter located in the at least one lumen of the outer catheter, the transporter catheter comprising a shaft;
a first balloon formed on the shaft and positioned adjacent to a distal end of the shaft;
at least a second balloon formed on the shaft and located between the first balloon and a proximal end of the shaft, the at least second balloon configured to anchor the transporter catheter to the outer catheter; and
wherein the transporter catheter is configured to be pushed thereby applying a pull force on the outer catheter to advance the outer catheter within a patient's vasculature and a component of the pull force reducing a frictional drag between the outer catheter and a wall of a vessel in a patient's vasculature by having the component of the pull force pulling a wall of the outer catheter away from the wall of the vessel in the patient's vasculature.

9. The catheter system of claim 8, wherein the shaft comprises at least one stiffening stylet for stiffening the shaft.

10. The catheter system of claim 8, wherein the shaft comprises a lumen to receive a guidewire.

11. The catheter system of claim 8, further comprising at least one imaging marker.

12. The catheter system of claim 8, wherein the shaft is tapered and the proximal end of the shaft has a diameter greater than a diameter of the distal end of the shaft.

13. The catheter system of claim 8, wherein the shaft comprises a plurality of segments having varying degrees of hardness.

14. The catheter system of claim 13, wherein a degree of hardness of the varying degrees of hardness of a segment of the shaft located between the first balloon and the at least second balloon is different from the degree of hardness of the varying degrees of hardness of a segment of the shaft located between the at least second balloon and the proximal end of the shaft.

15. A catheter system comprising: an outer catheter comprising at least one lumen; a transporter catheter located in the at least one lumen of the outer catheter, the transporter catheter comprising a shaft; a first balloon formed on the shaft and positioned adjacent to a distal end of the shaft; at least a second balloon formed on the shaft and located between the first balloon and a proximal end of the shaft, the at least second balloon upon inflation pressing against an inner surface of the at least one lumen of the outer catheter thereby anchoring the transporter catheter to the outer catheter; and wherein the outer catheter is configured to be pushed and/or torqued to advance simultaneously both the outer catheter and the transporter catheter within a patient's vasculature with both the first balloon and the at least second balloon fully inflated.

16. The catheter system of claim 15, wherein the shaft comprises at least one stiffening stylet for stiffening the shaft.

17. The catheter system of claim 15, wherein the shaft comprises a lumen to receive a guidewire.

18. The catheter system of claim 15, further comprising at least one imaging marker.

19. The catheter system of claim 15, wherein the shaft comprises a plurality of segments having varying degrees of hardness.

20. The catheter system of claim 19, wherein a degree of hardness of the varying degrees of hardness of a segment of the shaft located between the first balloon and the at least second balloon is different from the degree of hardness of the varying degrees of hardness of a segment of the shaft located between the at least second balloon and the proximal end of the shaft.

* * * * *